United States Patent
Groeber et al.

(10) Patent No.: US 10,066,983 B2
(45) Date of Patent: Sep. 4, 2018

(54) SENSOR SYSTEM FOR DETECTION OF PHASES AND/OR PHASE TRANSITIONS IN PERITONEAL DIALYSIS TREATMENTS

(71) Applicant: Fresenius Medical Care Deutschland GmbH, Bad Homburg (DE)

(72) Inventors: Tobias Groeber, Heusenstamm (DE); Peter Wabel, Darmstadt (DE); Sebastian Wieskotten, Erfelden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 65 days.

(21) Appl. No.: 15/024,362

(22) PCT Filed: Sep. 24, 2014

(86) PCT No.: PCT/EP2014/070342
§ 371 (c)(1),
(2) Date: Mar. 24, 2016

(87) PCT Pub. No.: WO2015/044185
PCT Pub. Date: Apr. 2, 2015

(65) Prior Publication Data
US 2016/0216150 A1    Jul. 28, 2016

(30) Foreign Application Priority Data

Sep. 28, 2013 (DE) .......... 10 2013 016 204

(51) Int. Cl.
*G01G 19/414* (2006.01)
*A61M 1/28* (2006.01)
*G01G 17/04* (2006.01)

(52) U.S. Cl.
CPC ............. *G01G 19/414* (2013.01); *A61M 1/28* (2013.01); *A61M 1/282* (2014.02); *A61M 1/288* (2014.02); *G01G 17/04* (2013.01); *A61M 2205/3331* (2013.01); *A61M 2205/3393* (2013.01); *A61M 2205/3553* (2013.01); *A61M 2205/3561* (2013.01); *A61M 2205/52* (2013.01); *A61M 2205/702* (2013.01)

(58) Field of Classification Search
CPC .................................................. G01G 18/414
USPC ....................................................... 73/432.1
See application file for complete search history.

(56) References Cited

U.S. PATENT DOCUMENTS

| | | | |
|---|---|---|---|
| 5,445,610 A | 8/1995 | Evert | |
| 6,196,992 B1 * | 3/2001 | Keilman | A61M 1/28 604/131 |
| 9,354,640 B2 * | 5/2016 | Byler | A61M 1/14 |

(Continued)

FOREIGN PATENT DOCUMENTS

| | | | |
|---|---|---|---|
| CA | 2223846 | 6/1999 | |
| CA | 2223846 A1 * | 6/1999 | A61M 1/28 |

(Continued)

*Primary Examiner* — Lisa Caputo
*Assistant Examiner* — Jamel Williams
(74) *Attorney, Agent, or Firm* — Jacobson Holman, PLLC.

(57) ABSTRACT

A sensor system of a medical system, in particular a manually operable, gravimetric system for continuous ambulant peritoneal dialysis (CAPD), provides for detection of a treatment status. In particular, the sensor system provides for detection of a phase segment and/or a phase transition during the peritoneal dialysis.

23 Claims, 2 Drawing Sheets

(56) References Cited

U.S. PATENT DOCUMENTS

| | | | |
|---|---|---|---|
| 2013/0172806 A1* | 7/2013 | Griessmann | A61M 1/282 604/28 |
| 2015/0005699 A1* | 1/2015 | Burbank | A61M 1/285 604/29 |
| 2016/0018347 A1* | 1/2016 | Drbal | A61M 1/288 210/647 |

FOREIGN PATENT DOCUMENTS

| | | | | |
|---|---|---|---|---|
| CN | 1893991 | | 1/2007 | |
| CN | 201453741 | | 5/2010 | |
| CN | 101745157 | | 6/2010 | |
| CN | 202136617 | | 2/2012 | |
| DE | 602004011981 | | 3/2009 | |
| EP | 0097432 | | 1/1984 | |
| WO | WO 96/37243 | | 11/1996 | |
| WO | WO 9637243 A1 * | | 11/1996 | A61M 1/28 |
| WO | WO 2014/109900 | | 7/2014 | |
| WO | WO 2014109900 A2 * | | 7/2014 | A61M 1/282 |

* cited by examiner

SENSOR SYSTEM FOR DETECTION OF PHASES AND/OR PHASE TRANSITIONS IN PERITONEAL DIALYSIS TREATMENTS

CROSS-REFERENCE TO RELATED APPLICATION

This application is the national stage of PCT/EP2014/070342, filed Sep. 24, 2014.

BACKGROUND OF THE INVENTION

1. Field of the Invention

The invention is directed to a sensor system of a medical system, in particular a manually operable, gravimetric system for continuous ambulant peritoneal dialysis (CAPD) for detection of a treatment status, in particular for detection of a phase segment and/or a phase transition in peritoneal dialysis.

2. Description of Related Art

Dialysis methods are widely used in the practice of medicine, where they serve to treat a variety of diseases and disorders. Dialysis methods are used for purifying blood in patients with acute or chronic renal insufficiency in various stages of the disease.

A fundamental distinction is made between extracorporeal dialysis processes (taking place outside of the body) and intracorporeal dialysis processes (taking place inside of the body). The extracorporeal processes include hemodialysis, hemofiltration and hemodiafiltration, while peritoneal dialysis is an intracorporeal process.

In hemodialysis, the patient's blood is purified through a filter having a special membrane, whereas the peritoneum functions in peritoneal dialysis as an endogenous filter membrane. In peritoneal dialysis, a dialysis solution is introduced into the abdominal cavity, absorbing the metabolic products, and is removed from the abdominal cavity after a certain dwell time.

Both manual and automatic methods are available for performing peritoneal dialysis. Continuous ambulant peritoneal dialysis (CAPD) is a manual method, in which the patient himself replaces the dialysis solution in the abdominal cavity several times a day. In automatic peritoneal dialysis (APD), the dialysis solution is exchanged through a device, a so-called cycler. APD is usually performed at night while the patient is asleep.

As already mentioned, CAPD is a manual method, which may be performed gravimetrically. However, the APD cycler may also be designed as a gravimetrically operated cycler.

For the control, monitoring and data acquisition of the PD treatment, the APD cycler is equipped with extensive mechanical systems such as pumps, valves and motors and with electronic systems such as sensors and data processing equipment, for example. The control of the cycler and in particular the determination of a current treatment status are based on the interaction of the aforementioned components for determining treatment-specific measured data, such as the volume, pressure, weight, flow rates and in comparison with a preset prescription for treatment.

The measured data thereby obtained can be processed in a data processing unit, which makes is possible to determine various dialysis parameters, which may also provide information about the duration of treatment and the goal of the treatment.

U.S. Pat. No. 5,445,610 describes a gravimetric PD cycler having a weighing cell, among other things. The weight measurements obtained using the weighing cell are compared with preset data in a computer and converted into corresponding volumes by means of a controller. This permits automatic control of the valves and a definition of the filling amounts, dwell amounts and drain amounts for each individual treatment cycle. In addition, the ultrafiltration amount can also be determined.

EP 0 097 432 also describes a gravimetric PD cycler having two scales. To achieve a defined filling volume, the bag weight of the first scale is compared with a preset value from the prescription for treatment until reaching said preset value. On reaching the preset weight on the scale, the valves are automatically activated and controlled at the same time. The drainage weight is detected by the second scale. The ultrafiltration weight and thus also the ultrafiltration volume can be determined from the filling weight and the drainage weight with the help of a computer.

CAPD systems that operate purely gravimetrically and are operated manually do not require any complex equipment in terms of equipment technology. These systems are therefore simple and inexpensive to manufacture and operate and are virtually trouble-free and maintenance-free in comparison with the other dialysis processes.

However, these systems require a high measure of personal responsibility and discipline on the part of each patient in performing the treatment and in maintaining the documentation.

SUMMARY OF THE INVENTION

The object of the present invention is therefore to provide a manually operable, gravimetric CAPD system, which, with little technical complexity, informs the patient of the current treatment status, in particular a phase segment and/or a phase transition during a cycle in the PD treatment and/or by means of instructions or information about the remaining course of treatment.

This object is achieved by the subject matter described herein. A sensor system, which is mounted on a manually operable, gravimetric CAPD system and can be used to measure a change, is provided and then this change can be used to infer the status of a dialysis treatment at a certain point in time, and the data can then be stored on a memory medium.

This object is also achieved by a method for measuring a change by means of a sensor system mounted on a manually operable, gravimetric CAPD system as described herein.

In addition, the object is achieved by a manually operable, gravimetric CAPD system with a sensor system for measuring a change as described herein.

Additional advantageous embodiments of the invention are also described herein.

CAPD systems used in the sense of the invention are systems which are manually operated and work according to a purely gravimetric principle, comprising at least one dialysis bag, which is preferably already filled with dialysis solution and is ready to use, at least one drainage bag, a device for controlling a fluid flow, a tubing system for connecting the bag to a catheter connection to the patient and a sensor system.

For the control of the individual fluid paths such as draining the spent dialysate out of the patient, scavenging the tubing system and filling the peritoneum with dialysate is performed according to the invention with the help of manually operable valves or clamping devices. The valves may be designed as one-way valves or multi-way valves, and the clamping devices may be designed as hose clamps, for example. The fluid is controlled manually by the patient or user.

The sensor system according to the invention may comprise at least two sensors, which may be connected to an evaluation unit, a display unit and/or a timing device, e.g., in the form of a timer, a stopwatch or a clock with time and date display and which have a connection to a memory medium. The sensor system is mounted on a manually operable, gravimetric CAPD system.

The sensors according to the invention may be optical sensors, pressure sensors, flow sensors, volume sensors and/or weight sensors.

In the sense of the invention, the evaluation unit serves to receive the measured data and/or measured signals for comparison of same, so that the individual phase segments and/or phase transitions in particular can be determined and thus allow an inference regarding the status of a dialysis treatment at a certain point in time, such that this status can be output via a display unit and the measured data or measured signals may be stored on a memory medium. A timer device is advantageously integrated into the evaluation unit.

BRIEF DESCRIPTION OF THE DRAWINGS

The subject matter of the present invention is explained in greater detail below with reference to the drawings.

DETAILED DESCRIPTION OF THE PREFERRED EMBODIMENTS

Figure 1:
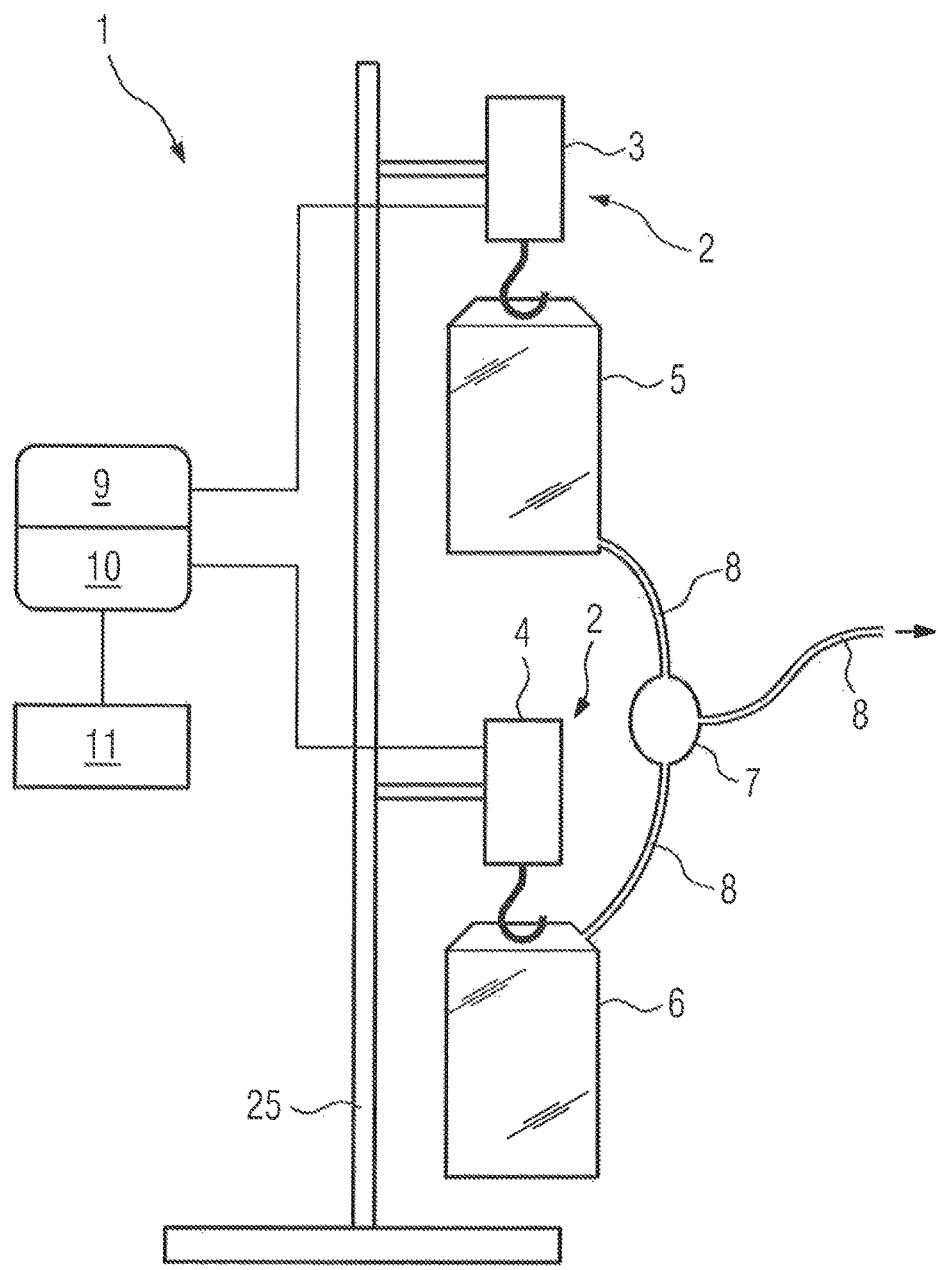
FIG. 1 shows the schematic design of a manually operable, gravimetric CAPD system according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Multiple cycles consisting of three phases are usually run through in peritoneal dialysis. The dialysis treatment begins with the drainage phase in a first step, in which the spent dialysate is drained out of the peritoneum. In a second step, the priming or scavenging phase is performed to scavenge air out of the tubing system with the dialysate from the dialysate bag. The solution for scavenging is sent directly into the drainage bag by means of the device for controlling the fluid flow. The filling phase, which is also referred to as the fill phase, is performed as the third step for filling the peritoneum with fresh dialysis solution. Depending on the prescription for treatment, the solution remains in the peritoneum for a certain period of time before the next cycle begins again with phase 1. This process is repeated several times a day in accordance with the prescription for treatment.

Peritoneal dialysis, in particular continuous ambulant peritoneal dialysis, which is well-suited for home dialysis because of its ease of operation and its low susceptibility to problems and little need for maintenance, nevertheless requires good training and a high level of personal responsibility and discipline on the part of the patient to perform the dialysis treatment and to maintain the documentation. In peritoneal dialysis, it is therefore advantageous if the current treatment status, in particular the phase segments and/or phase transitions, can be displayed. It is especially advantageous here if the patient receives instructions on how to proceed with the treatment on the basis of the measured data or signals obtained with the sensor system.

The information about a current treatment segment allows the patient to have a more rapid and better overview of the treatment status, in particular when his intervention is necessary. For example, the patient may be informed by means of a display unit that he is still in the drainage phase or drainage phase of his treatment and/or that this phase is not yet concluded and/or the end of the drainage phase may be displayed. It is possible in this way to prevent the patient from beginning the filling phase too early, so the filling volume in the peritoneum increases beyond a tolerable extent and results in overfilling of the patient. At the end of the drainage phase, there may be the instruction to the patient that he should now start the priming phase. In addition, at the end of the priming phase, the patient may be instructed to terminate it and to start the filling phase. At the end of the filling phase, the patient's attention may also be drawn by means of the display unit to the fact that, for example, a written display gives notice of the end of filling or a written display instructs the patient or user to perform the disconnection to terminate the treatment cycle. In a special embodiment, the end of each phase may be indicated by an acoustic signal, in particular on reaching the setpoint filling rate/filling volume, to signal the end of the treatment cycle.

The indication of the various phase segments and/or phase transitions during the treatment offers the patient improved convenience and greater safety without having to provide a complex technology. It is thus possible by means of the sensor system to recognize the treatment status without requiring a technologically complex actuator system. In addition, it is of crucial importance, especially in the priming phase, for this to be conducted for a sufficiently long period of time to remove all the air present in the tubing system. If the priming phase is ended too early, air from the tubing system enters the peritoneum, which can result in the pathological condition known as pneumoperitonitis. However, if the tubing system is scavenged for too long, there is the risk that not enough dialysate will be available for the actual treatment. In the case of manually operable, gravimetric CAPD systems, which are known from the prior art, the patient or user must himself recognize the proper time for the end of the priming phase. Through an instruction to terminate the priming phase, the patient's attention may be drawn to the need to switch to the next treatment step at the proper point in time.

For illustration, FIG. 1 shows schematically the design of a manually operable, gravimetric CAPD system (1) as an example, to which a sensor system (2) is attached and with which a change can be measured, said change allowing an inference as to the status of a dialysis treatment at a certain point in time, and the data being recordable on a memory medium (11). The sensor system (2) is characterized in that it is suitable for performing a flow rate measurement, a filling level measurement, a pressure measurement, a volume measurement and/or a weight measurement. To do so, the sensor system (2) may be equipped with optical sensors, pressure sensors, flow rate sensors, volume sensors and/or weight sensors. In addition, the sensor system (2) comprises at least two sensors (3, 4). A dialysate bag (5) is attached to a holding device (25) by means of a first sensor (3). Beneath the sensor bag (5) there is a drain bag (6), which is also attached to the holding device (25) by means of a second sensor (4). In a preferred embodiment, the sensors (3, 4) are weight sensors such as those used in electronic scales. The fluid flows are regulated according to the respective phases by means of a fluid control device (7). The fluid control device (7) controls the fluid flow between the dialysate bag (5), the drainage bag (6) and the abdominal connection to the patient through a tubing system (8). The sensor system (2) may also have a memory medium (11) on which the measured data and/or measured signals can be recorded.

The sensor system (2) is also connected to an evaluation unit (9). The data is acquired by means of the sensors (3, 4), wherein to determine a change in status of a dialysis treatment, the measured data or signals are relayed to the evaluation unit (9) by at least two sensors (3, 4). The measured data on the two sensors (3, 4) may be compared with one another at a certain point in time. The measured data from the two sensors (3, 4) may advantageously be detected at the same point in time and compared with one another at the same time by means of an evaluation unit (9). In addition, it is especially preferable to record the measured data of the at least two sensors (3, 4), which can be compared with one another continuously with the help of the evaluation unit. The measured data or signals determined on the basis of the sensors may be converted in an evaluation unit (9), so that they can be output on a display unit (10) as a phase segment and/or a phase transition at a certain point in time in a dialysis treatment. In another embodiment, instructions or a note may be output on the display unit (10) by means of the evaluation unit (9), indicating how to proceed with the treatment. To this end, the sensor system (2) is coupled to a timer device (not shown), for example, in the form of a timer or a stopwatch to be able to determine the phase segments and/or phase transitions as a function of time t. The timer device is advantageously integrated into the evaluation unit (9).

Figure 2:
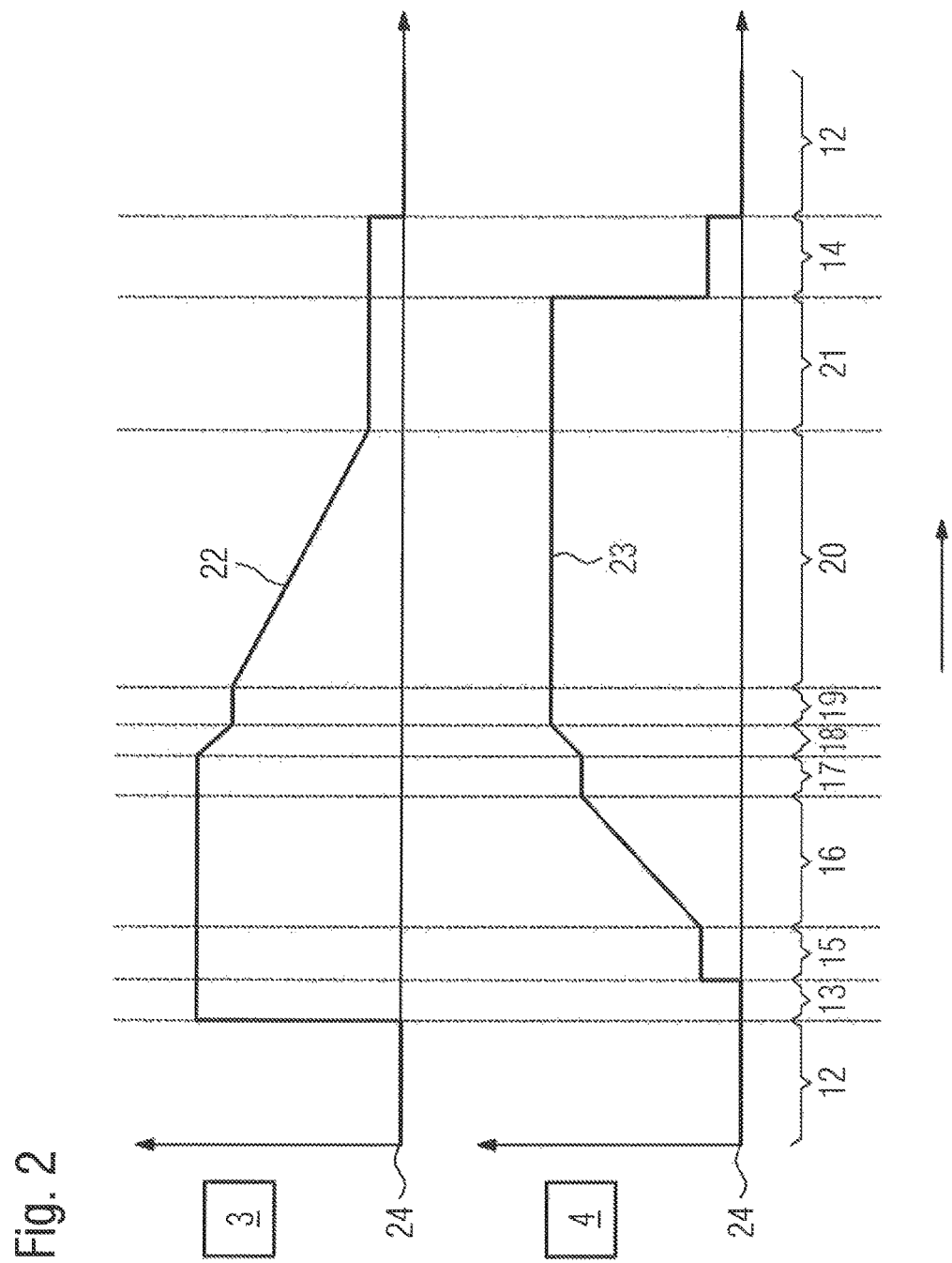
FIG. 2 shows a graphic diagram of the individual phase segments and phase transitions during a cycle of a CAPD treatment.

As shown in FIG. 2, for example, the following phase segments and/or phase transitions can be determined with the evaluation unit (9). Before the start of the treatment, i.e., when neither the dialysate bag nor the drainage bag has been hung in place, the CAPD system is in an unloaded state (12). An unloaded state (12) also occurs when the two bags (5, 6) have been removed after the treatment. The signals that are measured by means of the sensors (3, 4) change when one or more dialysate bags or drainage bags (5, 6) are connected or disconnected from the hanging attachment, so that the loading and unloading phases (13, 14) can be determined on the basis of the change in data. After loading, there is no further change in the data. The system is in a first phase transition (15). By means of the sensors (3, 4), it is also possible to check on whether the loading with the bags (5, 6) has been performed correctly, so that a mistake in operation can be ruled out in this way. The drainage phase (16) is initiated when the spent dialysate is drained out of the patient's peritoneum; this can also be determined from the ratio of the measured data of the sensors (3, 4). After the spent dialysate has been drained out of the peritoneum, another constant state is reached because no change in signal is recorded at either of the two sensors (3, 4), so that now a second phase transition (17) has been reached. This is followed by the scavenging phase or priming phase (18), wherein there is again a recognizable change in the signal at both sensors (3, 4). After the scavenging phase (18), a third phase transition (19) is reached, in which the measured data of the at least two sensors (3, 4) also do not change in relation to one another. The filling phase (20) begins when dialysate is introduced into the patient and is concluded as soon as all of the dialysate has run out of the dialysate bag (5) and/or the filling volume prescribed by the physician has been reached, and the measured value from the first sensor (3) no longer changes. The filling volume in the present example is detected by the sensors as the fill weight and can be converted to a volume value by an evaluation unit and then displayed. Next, the dwell phase begins, during which the dialysate remains in the peritoneum for a predetermined period of time. The dwell phase here is to be understood as the fourth phase transition (21), because during this phase, the dialysate remains in the patient and there is no fluid transfer and therefore there is no change in the signal on the sensors. With the unloading process, i.e., the removal of the bag, a zero point or starting point is again reached on the sensors (3, 4), as already described above. The phase transitions are characterized in particular in that no change in signal is detected on the two sensors (3, 4) over time t.

The individual phase transitions are between the phases described above and are represented as dashed vertical lines in FIG. 2. They may also be determined by means of the evaluation unit (9) on the basis of the change in the measured data and/or signals. The following phase transitions can be determined:

Beginning at the start of the loading operation (13) of the CAPD system (1) with one or more dialysate bags and/or drainage bags (5, 6) until reaching a first phase transition (15), wherein the first phase transition (15) occurs between the end of the loading process (13) and the start of the drainage phase (16), a second phase transition (17) between the end of the drainage phase (16) and the start of the scavenging and/or priming phase (18), a third phase transition (19) between the end of the scavenging phase (18) and the start of the filling phase (20), and a fourth phase transition (21) between the end of the filling phase (20) and the unloading phase (14) of the dialysis bags and/or drainage bags.

The display of the phase segments, phase transitions and/or measured data preferably appears in a numeric, written or symbolic representation on the display unit (10), for example, in the form of a display, a display screen or a monitor.

The measured data and/or signals detected in the treatment for determination of a current treatment phase and/or phase segment and/or a phase transition may be recorded on a memory medium (11) for storage and for possible further processing. This makes it easier for the patient to manage the documentation of his data. Then the data need not be recorded by hand in a data sheet and instead may be sent to the system for further analysis by a data processing system. The treating physician thus also has access to a well-founded data record on the basis of which he can track the course of treatment. In addition, therapy-relevant data can also be determined by using stored data from prior CAPD treatments. For example, the ultrafiltration volume can be calculated based on the current drainage weight/volume and the stored filling weight/volume. In addition, the fluid flow (change in volume per unit of time) can be determined from the measured data from the bag scales in the drainage phase, scavenging phase and/or filling phase. In particular the duration of the drainage phase or filling phase also allows conclusions to be drawn regarding the status of the patient's catheter. For the case when the patient's catheter is clogged or there is a kink in the catheter tubing, this leads to a definitely prolonged drainage phase and/or filling phase in comparison with previous treatments and/or the times which are stipulated in the prescription. By comparing the duration of time with the drain times and/or filling times from previous treatments or the times stipulated in the prescription for treatment, such sources of error can be detected and appropriate countermeasures may be initiated by the patient or user in response to a corresponding instruction on the display unit (10).

The various treatment volumes such as the drainage volume, the filling volume and the scavenging volume can also be calculated with the detection of the individual phase segments and/or phase transitions. These can be determined from the measured data of the at least two sensors, in particular the weight sensors of the bag scales, which are measured between the phase transitions and converted to a volume value in an evaluation unit. In this way, for example, the filling volume can be determined from the measured values for the phase transition between the start of filling and the phase transition at the end of filling.

The calculation and further processing of individual treatment parameters can be performed with the evaluation unit (9) coupled to the sensor system (2) as well as in external data processing systems.

For data storage, internal memory media (11) in the form of an internal hard drive may be provided or the data may preferably be stored on an interchangeable memory medium such as a readily portable memory medium in the form of a chip card, a USB stick, a rewriteable CD or similar data media, for example. The data may especially preferably also be transferred to external memory media, for example, in the form of an external hard drive, an external memory card or a data hub in a separate data processing device. The data may then be transferred to a cell phone, a PC, a laptop, a tablet or the like in a wireless or hardwired transmission and processed further there. In the case of a wireless data transmission to an external memory medium (11), the measured data may be transmitted, for example, by means of Bluetooth, W-Lan, ZigBee, infrared, optical transmission by means of QR code, acoustic data transmission or sound sequence, near-field communication or other suitable wireless communication devices.

It is self-evident that the memory media (11) have the corresponding accesses and connections as well as receiving devices for transmission and storage of the measured data.

In a particularly preferred embodiment, the measured data determined by a sensor system during a treatment by a sensor system (2) and recorded on a memory medium (11) may be used by means of an internal evaluation unit (9) or an external data processing device for calculation of individual treatment parameters and/or compared by comparison with measured data from previous treatments. Thus, for example, the measured data with regard to the ultrafiltration volume may be compared with data stored in the prescription for treatment or with the data from previous treatments to be able to detect changes and/or deviations from the desired therapeutic goal. In addition, possible trends with regard to various dialysis parameters which can be used for adjusting a future prescription for treatment (such as, for example, the filling volume, the ultrafiltration volume, dwell time) can be derived from previous treatments on the basis of the stored data. The measured data may also be used for error detection, as mentioned above, so that an incorrect load state, a catheter function state in the form of a clogged catheter connection or a kinked catheter tubing can be recognized, for example.

In another preferred embodiment, the manually operable, gravimetric CAPD system (1) may also be used to determine the transport capacity of the peritoneum (PDC=peritoneal dialysis capacity). For a PDC determination, it is relevant to determine the precise ultrafiltration volume, among other things. This is obtained from a differential measurement of the fresh dialysate in the dialysate bag and the spent dialysate drained off after the dwell time, including the liquid drained from the body. The dialysate bag usually has a larger filling volume than that given nominally in order to be able to ensure this nominal filling volume at the end of the storage time, so the actual dialysate volume at the point in time of the administration is not known precisely. The weight of the dialysate bag and the drainage bag (5, 6) in the filled and empty states, including the tubing set (8) with the fluid control device (7) can be determined by means of the sensors (3, 4) and then the exact ultrafiltration weight can be calculated from this data. The tubing set (8) with the fluid control device (7) is usually attached to the holder (25) at the start of the treatment and remains there even during the treatment, so that the weights are proportionally divided between the two sensors (3, 4). Changes in the ultrafiltration behavior can be detected by comparing the stored ultrafiltration weights from previous treatments. The ultrafiltration volume can be calculated from the differential weight on the basis of the density reported for the dialysate.

A method is described for measuring a change by means of a sensor system (2), which is mounted on a manually operable, gravimetric CAPD system (1), wherein the change allows the status of a dialysis treatment at a certain point in time to be inferred, and this data can be stored in a memory medium (11), with reference to a preferred exemplary embodiment, as depicted graphically in FIG. 2.

In the present example, the data acquisition is performed with two sensors (3, 4), wherein weight sensors such as those used with electronic scales are preferably used here. The data and/or signals measured at certain points in time are the first and second sensor (3, 4) is/are compared with one another by means of an evaluation unit (9). It is advantageous if the data is recorded and compared with one another at the same time. In an especially preferred embodiment, a curve (22, 23) is obtained by means of the two sensors (3, 4) and their continuous comparison over time in a continuous measurement of the weights for the dialysate bag (5) as well as for the drainage bag (6), wherein the two curves (22, 23) are compared with one another and converted in an evaluation unit (9) in order to be able to output a phase segment and/or a phase transition on a display unit (10) for a certain point in time. Thus, by evaluating the change in the measured data over time, it is possible to determine a signal trend (e.g., the signal remains the same, the signal declines or the signal increases) for a corresponding time window by evaluating the change in the measured data over time. In addition, a signal trend for a selected time window can be quantified on the basis of a curve (22, 23). At the start of the time axis, the two sensors (3, 4) are at a so-called zero point or starting value (24), which means that there is not yet a signal change to be recorded because the CAPD system has not yet received the bags (5, 6). During the loading operation with the filled dialysate bag, a sudden change in the first segment curve (22) can be observed and there is only a minor signal change due to the attachment of the drainage bag while still empty in the second curve (23).

Due to the sudden and offset change in the measurement signal, the evaluation unit (9) detects that the manually operable, gravimetric CAPE) system (1) is in the loading phase (13). Since there is no change in signal to be determined after the loading process, the evaluation unit (9) recognizes that the system is in its first phase transition (15). Because of the preceding measured data, instructions telling the patient to begin drainage can preferably be output to a display unit (10) by means of the evaluation unit (9) of the sensor system (2). If there is then an increase in the second curve (23) in the remaining course of the treatment and if there is no signal change in the first curve (22), the evaluation unit (9) recognizes that the CAPD system is in the drainage phase. Then the current phase segment of "drainage" can be displayed on the display unit (10). As soon as a signal change can no longer be measured either in the first or the second curve (22, 23), the evaluation unit (9) detects that the drainage process is concluded and a second phase transition (17) has been reached. Then an instruction, for example, to start a scavenging process, can be displayed optically on the display unit (10) during the scavenging phase (18). The scavenging phase (18) is detected by the evaluation unit (9) by the fact that the signal on the first sensor (22) declines and the signal on the second sensor (23) increases. In the case of a manually operable CAPD system (1), the patient automatically performs the initiation and performance of the individual phases himself, so the scavenging phase (18) is terminated by the patient when the tubing system is free of air. There is no further change in signal, and a third phase transition (19) has been reached.

At the end of the scavenging phase (18) (or the other phase segments and phase transitions), the attention of the patient or user may be drawn on the basis of the fluid flow or the fluid volume, for example, by instructing him to terminate the scavenging phase (18) by means of an optical display on the display unit or an acoustic signal. From the preceding measured data and/or signal trends for the at least two sensors (3, 4), it is possible by means of the evaluation unit (9) to derive the corresponding phase segments and/or phase transitions and to output an instruction to the patient to start the filling phase (20) in this stage of the treatment. By continuous recording of the measured data of the sensors (3, 4), a declining signal trend can be recognized in the filling phase for the first sensor (22), while the signal on the second sensor (23) does not change because the dialysate is introduced into the patient's peritoneum. Based on the comparison of the two curves (22, 23), the evaluation unit (9) detects the filling phase (20) and this can also be output as information about the current status by the display unit (10). The end of the filling phase (20) is reached when a constant signal is received by the first sensor (22) which (sensor or signal?) goes directly to the dwell phase. The dwell phase thus constitutes a fourth phase transition (21) because no signal change can be observed here on either the first sensor or the second sensor (3, 4). On reaching the fourth phase transition (21), the patient or user may be informed via the display unit (10) that now the disconnection may take place.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

Due to the removal of the bags (5, 6), there is a minor change in the signal on the first sensor (3) of the dialysate bag (5) and a much larger change in signal on the second sensor (4) of the drainage bag (6) because this bag is now filled. By comparing the two signal trends after the unloading process (14) and the prior phase information, the evaluation unit (9) detects that a zero point or starting value (24) and thus the end of a treatment cycle has been reached.

In a preferred embodiment, the timer device is started automatically after the filling phase to remind the patient to initiate a renewed drainage phase (16) and thus a new treatment cycle for triggering an alarm after a predetermined dwell time of the dialysis solution in the peritoneum has elapsed.

To achieve the most complete possible emptying of the peritoneum, after the end of drainage has been detected, an instruction may be issued to the patient, telling him to stand up and perform shaking movements and/or to wait for a while, so that any dialysate still running out can be drained before disconnection. The waiting time may usually be 1 to 15 minutes, preferably 5 to 10 minutes.

In another special embodiment, the point in time, in particular the date and the time of day of the CAPD treatment and/or of changing the bag can be recorded by means of a timing device, for example, in the form of a clock with a time and date display.

The current waiting time before disconnection may also be displayed by means of the timer device.

The data may be recorded internally on a data medium or transferred to a data medium in an external device. By means of the saved point in time of the last treatment and/or the bag replacement, it is possible to remind the patient or the user of the start of the next treatment and/or of the next bag replacement. This reminder may be in the form of an optical or acoustic signal, for example, an alarm or an SMS text or similar instructions, making it possible to virtually rule out the risk of forgetting to change the bag. If someone nevertheless fails to change a bag, then an alarm message may be sent to the treating physician or the care personnel by means of the stored point in time.

In addition, it is also possible to record the course of treatment and the measured data for documentation with the time of day and the date on a memory medium, for example, for a subsequent evaluation and further processing of the data by means of the timer device. In another preferred embodiment, the sensor system (2) may communicate with an external data acquisition and processing device which can also receive data from other devices. The other devices may include personal scales, a blood pressure meter or a body composition monitor (BCM), for example, which also communicate with the external data acquisition and processing device. The external data acquisition and processing device serves as a central data hub, which can in turn also send data to the external devices. However, the central data hub may also be a component of the sensor system (2), in particular the evaluation unit (9). By connecting other devices by means of a central data hub, it is possible to take into account a plurality of additional measured data that may provide information about the course of treatment and the therapeutic goal.

LEGEND 1 manually operable, gravimetric CAPD system
2 sensor system
3 first sensor
4 second sensor
5 dialysis bag
6 drainage bag
7 fluid control device 8 tubing system
9 evaluation unit
10 display unit
11 memory medium
12 unloaded state
13 loading phase
14 unloading phase
15 first intermediate phase
16 drain or drainage phase
17 second intermediate phase
18 scavenging and/or priming phase
19 third intermediate phase
20 filling or filling phase
21 fourth intermediate phase
22 first curve
23 second curve
24 starting point or zero point
25 holding device

What is claimed is:

1. A sensor system of a manually operable, gravimetric continuous ambulant peritoneal dialysis (CAPD) system for a dialysis treatment, said sensor system comprising:
a first weight sensor and a second weight sensor that measure a weight of, respectively, a first dialysis fluid, as a first measured weight, and a second dialysis fluid, as a second measured weight; and
an evaluation unit that evaluates the first measured weight and the second measured weight such that a phase segment and/or a phase transition at a certain point in time of the dialysis treatment is determinable based on the first measured weight and the second measured weight.

2. The sensor system according to claim 1, further comprising at least one of optical sensors, pressure sensors, flow rate sensors, and volume sensors.

3. The sensor system according to claim 1, wherein the evaluation unit compares the first measured weight and the second measured weight to determine a change in a status of the dialysis treatment at the certain point in time.

4. The sensor system according to claim 3, wherein the first measured weight and the second measured weight are compared with one another at a same time.

5. The sensor system according to claim 4, wherein the first measured weight and the second measured weight are compared with one another continuously.

6. The sensor system according to claim 3, further comprising a display unit, wherein the phase segments, the phase transitions, and/or the first measured weight and the second measured weight are output numerically, as a symbol or a text display, on the display unit.

7. The sensor system according to claim 1, wherein the evaluation unit converts the first measured weight and the second measured weight such that the phase segment and/or the phase transition is output on a display unit at a certain point in time of the dialysis treatment.

8. The sensor system according to claim 7, further comprising a timer device associated therewith.

9. The sensor system according to claim 8, wherein the timer device is integrated with the evaluation unit.

10. The sensor system according to claim 7, wherein the evaluation unit determines the phase segments of loading, unloading, drainage, scavenging and/or filling, the phase transitions, and the unloaded states.

11. The sensor system according to claim 7, wherein the evaluation unit determines the phase transitions between a loading phase and a drainage phase, a drainage phase and a scavenging phase, a scavenging phase and a filling phase, and/or a filling phase and an unloading phase.

12. The sensor system according to claim 1, wherein the first measured weight and the second measured weight are recorded on a memory medium.

13. The sensor system according to claim 12, wherein the memory medium is an internal memory medium configured as an internal hard drive, or as a replaceable memory medium configured as a chip card, a USB stick, or a rewriteable CD, or as an external memory medium configured as an external hard drive or an external memory card or a data hub in a separate data processing device.

14. The sensor system according to claim 13, wherein the first measured weight and the second measured weight that are recorded on the memory medium are transmitted to the memory medium by hardwired or wireless data transmission.

15. The sensor system according to claim 14, wherein the wireless data transmission is by Bluetooth, W-Lan, ZigBee, infrared, optical transmission by QR code, acoustic data transmission by tone sequence, or near-field communication.

16. The sensor system according to claim 12, wherein the memory medium is an internal memory medium, or a replaceable memory medium, or an external memory medium.

17. The sensor system according to claim 16, wherein the external memory medium transmits the first measured weight and the second measured weight to a separate data processing device.

18. The sensor system according to claim 1, further comprising an internal evaluation unit or an external data processing device for error detection, for calculation of at least individual treatment parameters, and/or by comparison with the first measured weight and the second measured weight from previous dialysis treatments.

19. A method of measuring a change with a sensor system of a manually operable, gravimetric continuous ambulant peritoneal dialysis (CAPD) system for a dialysis treatment, said method comprising the steps of:
measuring with a first weight sensor and a second weight sensor, respectively, a first dialysis fluid, as a first measured weight, and a second dialysis fluid, as a second measured weight; and
evaluating with an evaluation unit the first measured weight and the second measured weight such that a phase segment and/or a phase transition at a certain point in time of the dialysis treatment is determinable based on the first measured weight and the second measured weight.

20. The method according to claim 19, further comprising a step of recording the first measured weight and the second measured weight at the certain point in time, and wherein the step of evaluating includes comparing the first measured weight and the second measured weight with one another.

21. The method according to claim 20, wherein the step of recording the first measured weight and the second measured weight is effected at a same time.

22. The method according to claim 21, wherein the step of recording the first measured weight and the second measured weight is effected continuously, and wherein the step of evaluating by comparing the first measured weight and the second measured weight with one another is effected continuously.

23. The method according to claim 20, wherein the step of evaluating includes generating a first curve and a second curve associated with, respectively, the first measured weight and the second measured weight, comparing the first sensor curve and the second sensor curve with one another, and converting the first sensor curve and the second sensor curve to signals that output the phase segment and/or the phase transition on a display unit for the certain point in time.

* * * * *